US010076621B2

(12) United States Patent
Robinson et al.

(10) Patent No.: US 10,076,621 B2
(45) Date of Patent: Sep. 18, 2018

(54) METHOD AND SYSTEM FOR DISPLAYING INFORMATION ON LIFE SUPPORT SYSTEMS

(75) Inventors: Scott William Robinson, Bayside, WI (US); Jonathan Robert Polhamus, Waukesha, WI (US); Paul David Hunsicker, Hales Corners, WI (US)

(73) Assignee: General Electric Company, Schenectady, NY (US)

( * ) Notice: Subject to any disclaimer, the term of this patent is extended or adjusted under 35 U.S.C. 154(b) by 1155 days.

(21) Appl. No.: 13/418,001

(22) Filed: Mar. 12, 2012

(65) Prior Publication Data

US 2013/0235080 A1 Sep. 12, 2013

(51) Int. Cl.
*A61M 16/00* (2006.01)
*G16H 40/63* (2018.01)
*A61M 1/36* (2006.01)
*A61B 6/00* (2006.01)
*G06F 19/00* (2018.01)

(52) U.S. Cl.
CPC ........... *A61M 16/022* (2017.08); *A61B 6/463* (2013.01); *A61B 6/563* (2013.01); *A61M 1/3666* (2013.01); *A61M 16/021* (2017.08); *G06F 19/3481* (2013.01); *G16H 40/63* (2018.01); *A61M 2205/3584* (2013.01); *A61M 2205/502* (2013.01)

(58) Field of Classification Search
CPC ...... G06Q 50/22; G06Q 50/24; G06F 19/322; G06F 19/3418; G06F 19/3406; G06F 19/327; G06F 19/324; G06F 19/321; G06F 19/3468; A61M 2205/502; A61M 2205/3584; A61M 16/021; A61M 16/022; G16H 40/63; G16H 10/60; G16H 15/00; G16H 20/13; G16H 30/20
USPC ........................................................ 705/2, 3
See application file for complete search history.

(56) References Cited

U.S. PATENT DOCUMENTS

| | | | |
|---|---|---|---|
| 7,567,651 B2 | 7/2009 | Serceki et al. | |
| 2001/0041991 A1* | 11/2001 | Segal et al. | 705/3 |
| 2003/0014817 A1* | 1/2003 | Gallant et al. | 5/600 |
| 2004/0003813 A1* | 1/2004 | Banner | A61B 5/0205 128/204.21 |
| 2004/0078231 A1* | 4/2004 | Wilkes et al. | 705/2 |
| 2004/0176983 A1* | 9/2004 | Birkett et al. | 705/2 |
| 2004/0249673 A1* | 12/2004 | Smith | 705/2 |
| 2007/0129647 A1* | 6/2007 | Lynn | 600/538 |
| 2008/0040160 A1* | 2/2008 | Scherpbier et al. | 705/3 |
| 2010/0177100 A1* | 7/2010 | Carnes et al. | 345/440 |
| 2010/0198622 A1* | 8/2010 | Gajic et al. | 705/3 |
| 2011/0019800 A1* | 1/2011 | Spahn | A61B 6/4233 378/98 |
| 2011/0071414 A1* | 3/2011 | Heil et al. | 600/511 |

(Continued)

*Primary Examiner* — Jonathan W Durant
(74) *Attorney, Agent, or Firm* — Dean D. Small; The Small Patent Law Group, LLC

(57) ABSTRACT

Methods and systems for displaying information on life support systems (LSS) are provided. One LSS includes a patient monitoring portion configured to acquire, as LSS information, patient measurement information from a monitored patient. The LSS also includes a communication device configured to communicate with a remote device to obtain, as non-LSS information, information acquired by the remote device. The LSS further includes a display configured to display a user interface that presents the non-LSS information.

25 Claims, 7 Drawing Sheets

(56) References Cited

U.S. PATENT DOCUMENTS

| | | |
|---|---|---|
| 2011/0072381 A1* | 3/2011 | Gannon et al. ............... 715/771 |
| 2011/0138308 A1 | 6/2011 | Palmer et al. |
| 2011/0154241 A1 | 6/2011 | Skidmore et al. |
| 2012/0278099 A1* | 11/2012 | Kelly et al. ........................ 705/3 |
| 2012/0323591 A1* | 12/2012 | Bechtel et al. ................... 705/2 |

* cited by examiner

METHOD AND SYSTEM FOR DISPLAYING INFORMATION ON LIFE SUPPORT SYSTEMS

BACKGROUND OF THE INVENTION

The subject matter disclosed herein relates generally to user interfaces for medical systems, and more particularly, to operator interfaces for medical systems, especially life support systems, and the display of information by the interfaces.

Medical imaging systems may include different devices that acquire and display different types of information. For example, life support devices, such as respiratory care systems (e.g., mandatory mechanical ventilation systems) display information to allow for monitoring of a patient and to control the setting of different parameters, such as to mechanically ventilate the patient. In these life support systems, patient information from other devices may be needed or useful. However, often this information is not readily accessible or available for operators of life support systems. For example, the desired or needed information may be stored in remote archives, which results in delay in the clinical decision making process. Thus, the overall effectiveness of the life support systems may be reduced because of the capabilities available on the clinician-ventilator-patient interface.

SUMMARY OF THE INVENTION

In one embodiment, a life support system (LSS) is provided that includes a patient monitoring portion configured to acquire, as LSS information, patient measurement information from a monitored patient. The LSS also includes a communication device configured to communicate with a remote device to obtain, as non-LSS information, information acquired by the remote device. The LSS further includes a display configured to display a user interface that presents the non-LSS information.

In another embodiment, a method for presenting data using a life support system (LSS) is provided. The method includes receiving by the LSS, as non-LSS information, information from a remote device and providing access to the non-LSS information via the LSS. The method also includes displaying the non-LSS information on a display of the LSS.

In yet another embodiment, a non-transitory computer readable storage medium for displaying information with a life support system (LSS) using a processor is provided. The non-transitory computer readable storage medium includes instructions to command the processor to receive by the LSS, as non-LSS information, information from a remote device, provide access to the non-LSS information via the LSS and display the non-LSS information on a display of the LSS.

DETAILED DESCRIPTION OF THE INVENTION

Figure 1:
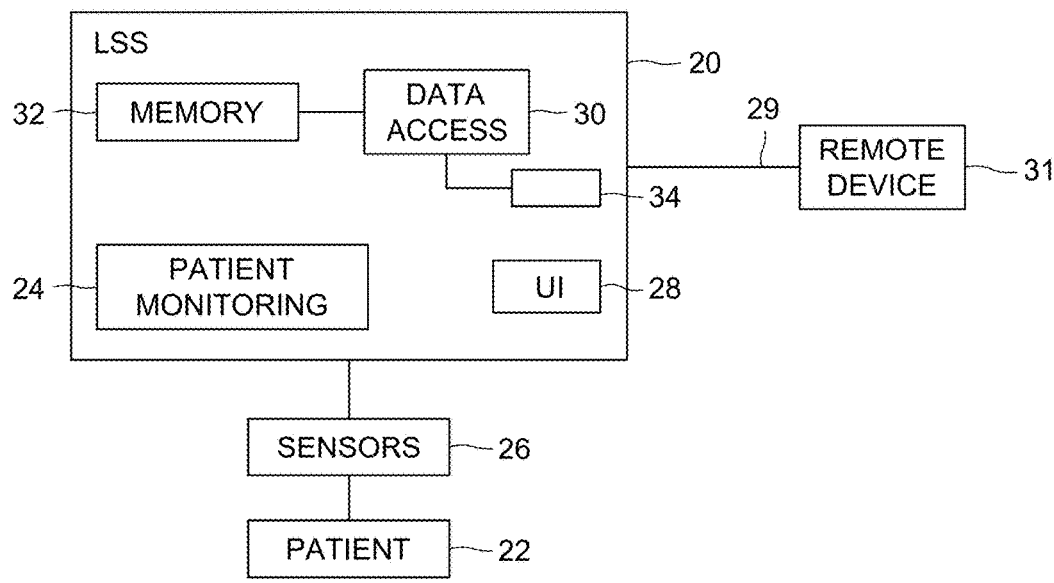
FIG. 1 is a simplified block diagram of a life support system formed in accordance with various embodiments.

The following detailed description of certain embodiments will be better understood when read in conjunction with the appended drawings. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

Various embodiments provide a medical system, which may be a life support system that allows access and display of information to a user that may be used in the treatment of a patient. For example, in some embodiments, a user interface for a life support system is provided that allows access and display of information from other devices (e.g., imaging devices), such as images acquired by an imaging scanner (e.g., x-ray machine). At least one technical effect of various embodiments is the ability to display and view information on a life support system acquired by a different medical device (also referred to herein as non-life-support system (non-LSS) information). At least one other technical effect of various embodiments is increasing the speed of the clinical decision making process and/or accelerating the caregiving process.

Various embodiments provide a medical system as shown in FIG. 1, which is illustrated as a life support system (LSS) 20. For example, the LSS 20 may be a patient monitoring system that provides mechanical ventilation of a patient 22 as described in more detail herein. The LSS 20 includes a patient monitoring module 24 that monitors the patient 22. In the illustrated embodiment, the patient monitoring module 24 acquires monitoring information (e.g., measurements) via one or more sensors 26. The LSS 20 also includes a user interface (UI) 28 that allows an operator to view the monitoring information and setting information to allow control of different parameters (e.g., ventilation parameters) for the treatment of the patient 22. The UI 28 may be provided in combination with any type of display device, such as a flat touch-screen display operable by touching the screen instead of using a physical keyboard. For example, the UI 28 may provide an onscreen virtual keyboard and also allows use of a passive stylus pen or a digital pen. However, in other embodiments, the UI 28 is provided in combination with a monitor and that includes a separate user interface with physical input controls.

The UI 28 also displays non-LSS information, such as non-LSS patient information that is obtained and/or stored in a data access module 30. For example, the data access module 30 may allow the operator to access and view images, such as x-rays (e.g., chest X-rays or radiology reports) of the patient 22 directly via the UI 28. The data access module 30 may be implemented in hardware, software, or a combination thereof to provide configurable access to information related to the patient 22. For example, medical images of the patient or corresponding medical reports (e.g., lab reports) may be stored in a memory 32 that can be accessed for display using the UI 28. In general, the data access module 30 provides access to any relevant patient information, which may be obtained through a wired connection or a wireless connection 29 with one or more remote devices 31, such as a hospital data management system or an imaging scanner (e.g., portable x-ray machine). Thus, the data access module 30 may acquire and display (as well as store) relevant patient information that is initially acquired or stored remote from the LSS 20. For example, the data access module 30 may access information from an Electronic Medical Records (EMR) system, an Electronic Health Records (EHR) system, and/or a Radiology Information System (RIS) system, among others.

The data access module 30 in various embodiments includes or is coupled to a communication device 34 for communicating with the remote device(s) 31 to obtain the patient information. For example, the communication device 34 may allow bi-directional communication between the LSS 20 and other medical systems or devices. The communication device 34 may include, for example, a transmitter and receiver arrangement for communication. It should be noted that any suitable wired or wireless communication technology may be used. For example, a wired cable connected through a port may provide access to a local area network (LAN) or a wide area network (WAN). Different wireless communication technologies may be used, such as a device to device communication method (e.g., Bluetooth, Infrared control, radio frequency control, etc.), which may be used to create a personal area network, or a broadcast type of communication method (e.g., WiFi, network, etc.). In various embodiments, the communication scheme or method allows secure communication, such as within a room of a hospital or to a remote medical systems or device(s) 31. The communication device 34 in some embodiments may be configured for mobile communications, such as using third generation (3G) or fourth generation (4G) mobile communication standards to communicate directly with a mobile communication device, such as a cell phone or tablet device.

Figure 2:
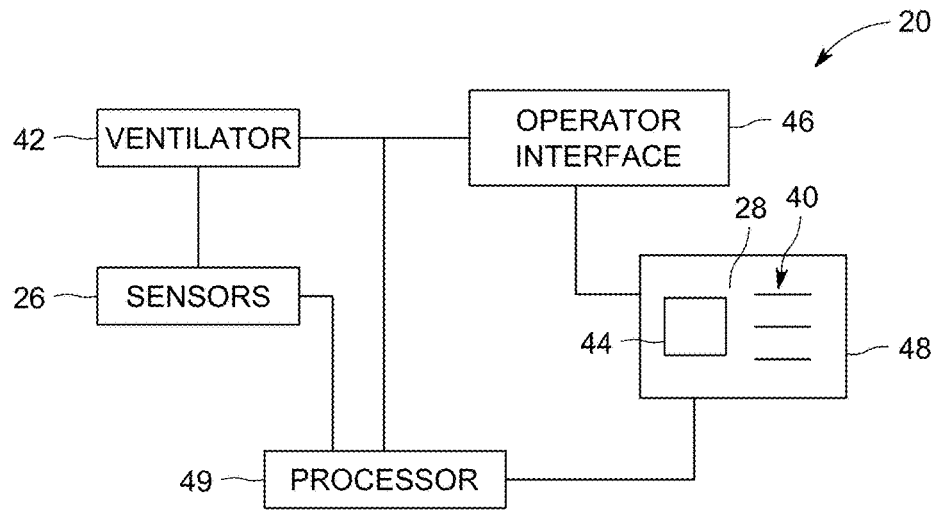
FIG. 2 is a simplified block diagram of one embodiment of a life support system illustrated as a patient monitoring system.

In various embodiments, the LSS 20 is embodied as a patient monitoring system providing mechanical ventilation as shown FIG. 2. In this embodiment, the LSS 20 provides for mechanically ventilating the patient 22 (shown in FIG. 1). The UI 28 provides for the visualization of the patient ventilation parameters that may be used to control a ventilator 42 based on displayed compliance data in combination with measurement data from the one or more sensors 26. The UI 28 also provides for visualization of other patient information 44, such as image(s) of the patient 22 or medical reports for the patient obtained by the data access module 30 (shown in FIG. 1).

The operation of the LSS 20, including the operation of the ventilator 42 may be controlled via an operator interface 46 by a clinician viewing the visualized patient ventilation parameter data, and other patient relevant data, which may be multiple data types displayed concurrently on a monitor 48, which may provide touch screen operation as described herien. In some embodiments, the operator interface 46 or a portion thereof may be part of the UI 28, for example, embodied as a virtual keyboard displayed on the monitor 48. The operator interface 46 may include different types of physical controls, such as a keyboard, mouse, trackball, buttons, knobs and/or switches, among other controls.

A processor, for example, a processing subsystem 49 may process received measurements from the sensors 26 and other compliance information to update the monitor 48 with patient ventilation parameter data. The processing subsystem 49 may also process received non-LSS information. The processing subsystem 49 may also embody the data access module 30 in some embodiments.

Figure 3:
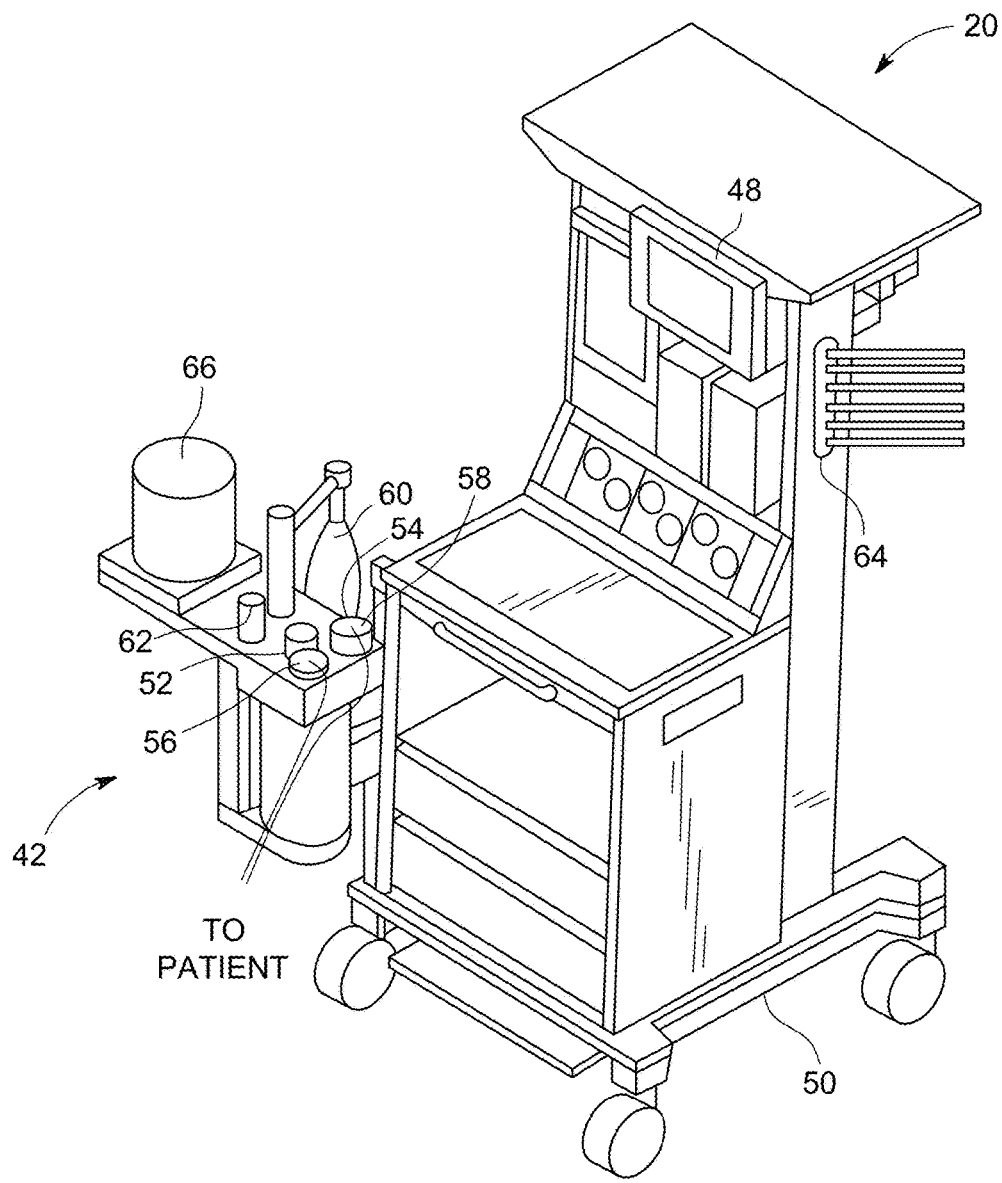
FIG. 3 is a front perspective view of an anesthesia machine formed in accordance with various embodiments

In one embodiment, the LSS 20 may be provided as an anesthesia machine 50 as shown in FIG. 3 that includes the ventilator 42 having suitable connectors 52, 54 for connecting to an inspiratory branch 56 and expiratory branch 58 of a breathing circuit leading to the patient 22 (shown in FIG. 1). The ventilator 42 and breathing circuit cooperate to provide breathing gases to the patient 22 via the inspiratory branch 56 and to receive gases expired by the patient 22 via the expiratory branch 58.

The ventilator 42 also optionally can be provided with a bag 60 for manually ventilating the patient 22. For example, the bag 60 can be filled with breathing gases and manually squeezed by a clinician (not shown) to provide appropriate breathing gases to the patient 22. Using this bag 60, or "bagging the patient," enables clinicians to manually and/or immediately control delivery of the breathing gases to the patient 22. The clinician can also sense conditions in the respiration and/or lungs of the patient 22 according to the feel of the bag 60, and then accommodate for the same. The ventilator 42 can also provide a toggle 62 for switching and/or alternating between manual and automated ventilation when the bag 60 is provided.

The ventilator 42 further can receive inputs from the sensors 26 (shown in FIGS. 1 and 2) associated with the patient 22 (e.g., coupled to the patient 22) and/or the ventilator 42 at a processing terminal 64 for subsequent processing thereof, and which can be displayed on the monitor 48. Representative data received from the sensors 26 can include, for example, inspiratory time ($T_I$), expiratory time ($T_E$), natural exhalation time ($T_{EXH}$), respiratory rates (f), I:E ratios, positive end expiratory pressure (PEEP), fractional inspired oxygen ($F_IO_2$), fractional expired oxygen ($F_EO_2$), breathing gas flow (F), tidal volumes ($V_T$), temperatures (T), airway pressures ($P_{aw}$), arterial blood oxygen saturation levels ($S_aO_2$), blood pressure information (BP), pulse rates (PR), pulse oximetry levels ($S_pO_2$), exhaled $CO_2$ levels ($F_{ET}CO_2$), concentration of inspired inhalation anesthetic agent ($C_I$ agent), concentration of expired inhalation anesthetic agent ($C_E$ agent), arterial blood oxygen partial pressure ($P_aO_2$), arterial carbon dioxide partial pressure ($P_aCO_2$), and the like.

Thus, the ventilator 42 provides breathing gases to the patient 22 via the breathing circuit. The monitor 48 allows an operator to view ventilator information, as well as patient information from remote devices or systems as described in more detail herein. For example, the monitor 48 may allow an operator to control the various pneumatic elements of the pneumatic circuitry that may also include a source of pressurized gas (not shown), which can operate through a gas concentration subsystem (not shown) to provide the breathing gases to the lungs of the patient 22. The pneumatic circuitry may provide the breathing gases directly to the lungs of the patient 22, as typical in a chronic and/or critical care application, or the pneumatic circuitry may provide a driving gas to compress a bellows 66 containing the breathing gases, which can, in turn, supply the breathing gases to the lungs of the patient 22, as typical in an anesthesia application.

Figure 4:
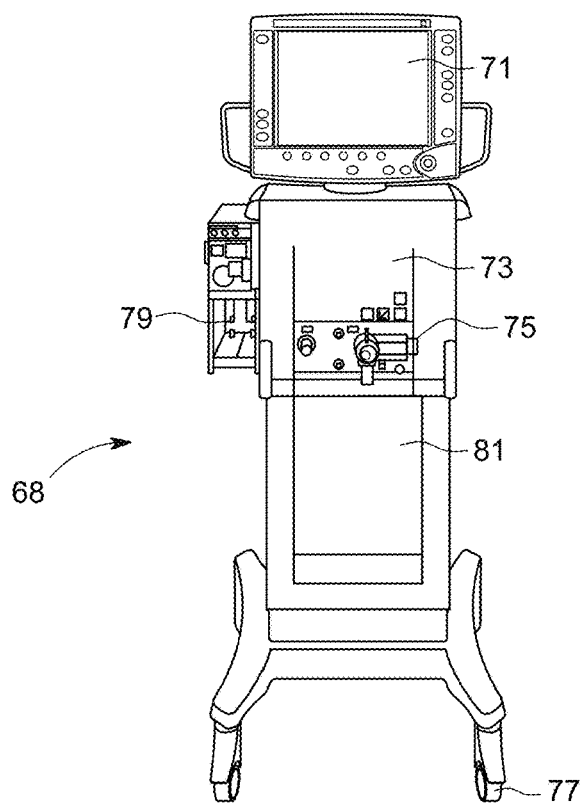
FIG. 4 is a front perspective view of a ventilator machine formed in accordance with various embodiments
Figure 5:
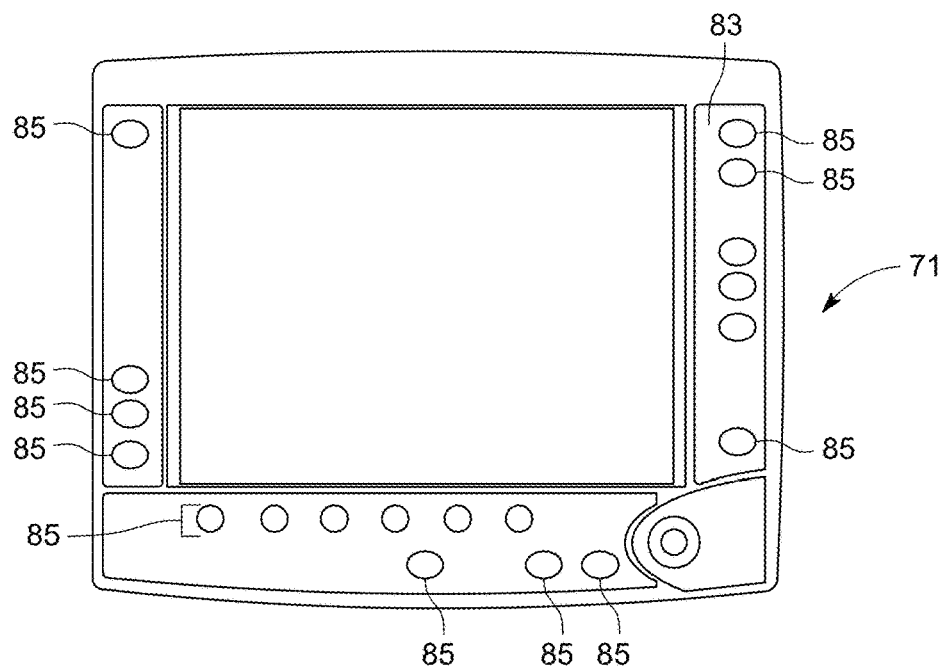
FIG. 5 is a diagram of a display of the ventilator machine of FIG. 4.

In another embodiment, the LSS 20 may be provided as a ventilator machine 68 as shown in FIGS. 4 and 5. For example, the ventilator machine 68 may be a bedside ventilator that provides breathing for the patient 22 (shown in FIG. 1). The ventilator machine 68 includes a display 71 (which may be embodied as the monitor 48) mounted on a ventilator unit 73 that provide oxygen to the patient 22 through a closed tubular circuit. A plurality of suitable connectors 75, which may include, for example, an inspiratory port and an expiratory port are also provided. However, it should be noted that other connectors 75 may be provided as desired or needed. The ventilator machine 68 may include wheels 77 allowing for movement of a cart 81 on which the ventilator unit 73 is supported. A module bay 79 optionally may be provided for receiving different modules to provide different functionality to the ventilator machine 68. It should be noted that the ventilator machine 68 may have similar components to the ventilator 42 shown in FIG. 3. Additionally, the ventilator unit 73 includes suitable processing components or processing machines as described herein.

In operation, and for example, respiratory therapists may monitor patient performance and adjust ventilator settings as appropriate using the display 71, which may include displaying the UI 28 as described in more detail herein. The display 71 may be any suitable type of display and may also provide touch screen functionality as described in more detail herein. The display also generally includes indicators 83 (e.g., LED alarms) and user inputs, such as a plurality of buttons 85 that may be programmable to provide different functions and a multi-function control 87 that is capable of receiving different user inputs (e.g., depression and rotation).

The UI 28 of various embodiments provides a viewer that is a user interface tool for the LSS 20, and specifically for controlling operation of the LSS 20, for example, the ventilator 42. For example, the UI 28 enables a user, such as a clinician, to balance and evaluate the patient ventilation parameters, while viewing patient information from a non-LSS system, such as images (e.g., chest x-rays) of or reports for the patient 22. Thus, the UI 28 allows control of one more ventilator parameters or settings based on displayed information, which may be related in part to patient physiology, as well as based on other clinically relevant patient information.

For example, medical images, in particular x-ray images, are useful in the treatment of patients on the ventilator 42. In various embodiments, the UI 28 provides images, which may be x-ray images, such as on the monitor 48 of the ventilator 42. Different types of information also may be accessible and displayable, such as a corresponding radiologist report when available as described in more detail herein, which will be in the context of or correspond to the associated x-ray image.

Figure 6:
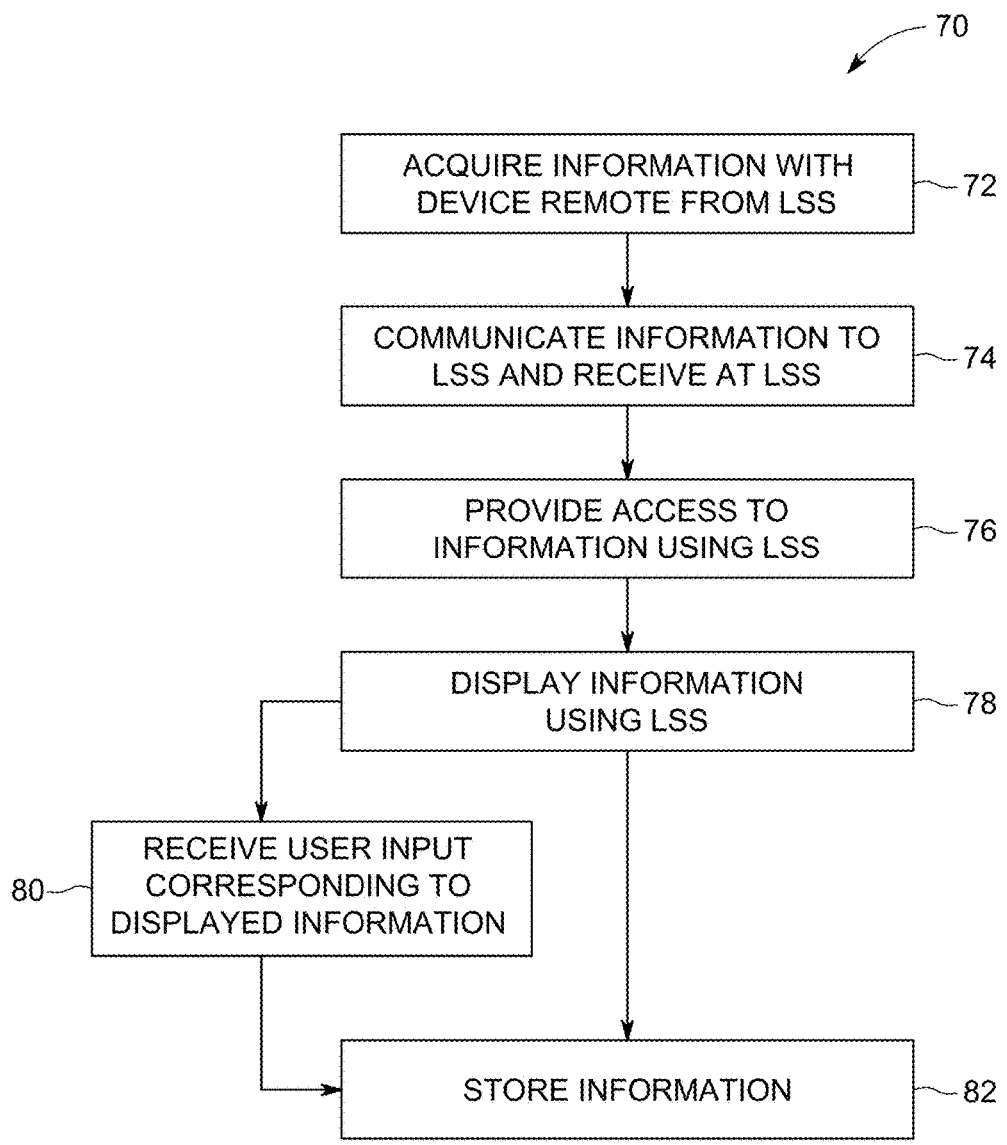
FIG. 6 is a flowchart of a method for acquiring and visualizing patient information on a life support system in accordance with various embodiments.

Accordingly, various embodiments provide a method 70 as shown in FIG. 6 for acquiring and visualizing patient information on the LSS system 20, wherein the patient information is not acquired by the LSS. In particular, the method 70 includes acquiring information at 72 with a device remote from the LSS. It should be noted that in various embodiments the term remote refers to any device that does not form part of the LSS. Accordingly, the device may be located adjacent to or in the same room as the LSS, or in a different room, such as in the hospital, or at a different building or location. For example, the information may be one or more x-rays acquired by taking the patient to a radiology department, or by use of a mobile x-ray device that is brought to the patient.

The information acquired remote from the LSS is received by the LSS, such as communicated to the LSS at 74 from the remote device. It should be noted that the information may be stored temporarily or permanently by the remote device acquiring the information, by an archive system (that the remote device may communicate with) before communicating the information to the LSS or may not be stored in the remote device and communicated directly to the LSS. For example, patient x-ray images may be communicated to the LSS by a data network, a USB device, wirelessly or by any similar data exchange process. It should be noted that when a mobile x-ray device is brought to the patient, and an x-ray is taken to acquire x-ray images, a defined workflow may be provided to transfer the images to the LSS before leaving the patients room. For example, the operator may be prompted to transfer the x-ray image(s) to the LSS and select the mode of communication.

The information communicated to the LSS, for example, patient information such as the x-ray image(s) are then accessible using the LSS at 76. For example, as described in more detail herein, a UI may be provided that allows access to and then display of the information at 78 using the LSS. The information may be displayed simultaneously, concurrently or sequentially with LSS information (e.g., patient ventilator information). For example, x-ray image(s) or a radiologist report may be displayed at the same time on the same screen as ventilator information. Accordingly, in one embodiment, x-ray information for the patient, regardless of how the information is acquired, can be accessed and reviewed using the LSS, for example, on a monitor of a patient monitoring system, for example, a ventilator system. In the case of images, the information may be based on a digital x-ray or a non-digital x-ray. A user also may be able to adjust some of the settings for the displayed image or annotate the displayed image as described in more detail below.

It should be noted that the displayed information at 78 may include different types and/or combinations of information. For example, a displayed x-ray image of the patient may be annotated by a reviewing radiologist, such that text or images are provided in combination with displayed image. In this example, the radiologist may review the x-ray(s) of the patient an annotate regions of interest, which can include highlighting (e.g., using a circle or square) a portion of the image to which the radiologist wants attention drawn. It should be noted that various embodiments provide a portal that may be used to display different types of information, which may also include different types of care information, for example, sections from the EMR, lab results, etc.

Additionally, the UI at the LSS may allow for user inputs corresponding to the displayed information. Accordingly, at 80, one or more user inputs corresponding to the displayed information may be received. For example, a respiratory physician viewing displayed x-ray images on the LSS may annotate or add comments to the image(s), which are then stored with the image(s) at 82. For example, the respiratory physician may leave electronic notes for the respiratory physician that will have the next shift monitoring the patient (e.g., typing notes into an electronic file stored in the LSS). However, the information received at the LSS and associated with the image also may be communicated from the LSS, such as forwarded in an email directly from the LSS or communicated to the hospital network. Thus, the image(s) with the annotations from the respiratory physician may be communicated to other caregivers at other locations (e.g., general medical practitioners or specialist). Accordingly, various embodiments provide the LSS with a type of social networking functionality.

The information stored at 82 at the LSS, which may be a short term storage to allow viewing of the information, or long term storage, allows subsequent access and viewing of the information. Accordingly, the memory or storage of the LSS in one embodiment allows for storing the information for subsequent access, for example, storing a set of x-ray images that may be acquired at the same time or at different times. It should be noted that the information may be stored initially when received from the remote device and then resaved after being modified locally at the LSS (e.g., annotated at the LSS), which may overwrite the existing stored image(s) or may be stored as new image files.

Different embodiments of the UI 28 will now be discussed. It should be noted that the UI 28 in various embodiments provides a viewer that allows an operator to view different types of information using the LSS, for example, LSS acquired information and non-LSS acquired information, such as patient images and reports from other clinicians (e.g., a radiologist report). The UI 28 may provide, for example, different functionality, such as tools to select and review the images. For example, the UI 28 may include a set of review tools such as, but not limited to, zoom, pan, adjust, contrast, brightness, etc. controls.

The UI 28 in various embodiments provides for access to information, such as patient information (e.g., x-ray images) that was acquired by a device other than the LSS 20. For example, the UI 28 provides access at the LSS 20 to patient x-rays for review directly on the LSS 20. Accordingly, various embodiments provide visualization of LSS information (e.g., ventilator settings and measurements) and non-LSS information on the LSS 20. The UI 28 provides an interface tool to control the LSS 20, including displaying different types of information to evaluate, for example, when determining a proper course of action, such as setting or modifying patient ventilation parameters.

Figure 7:
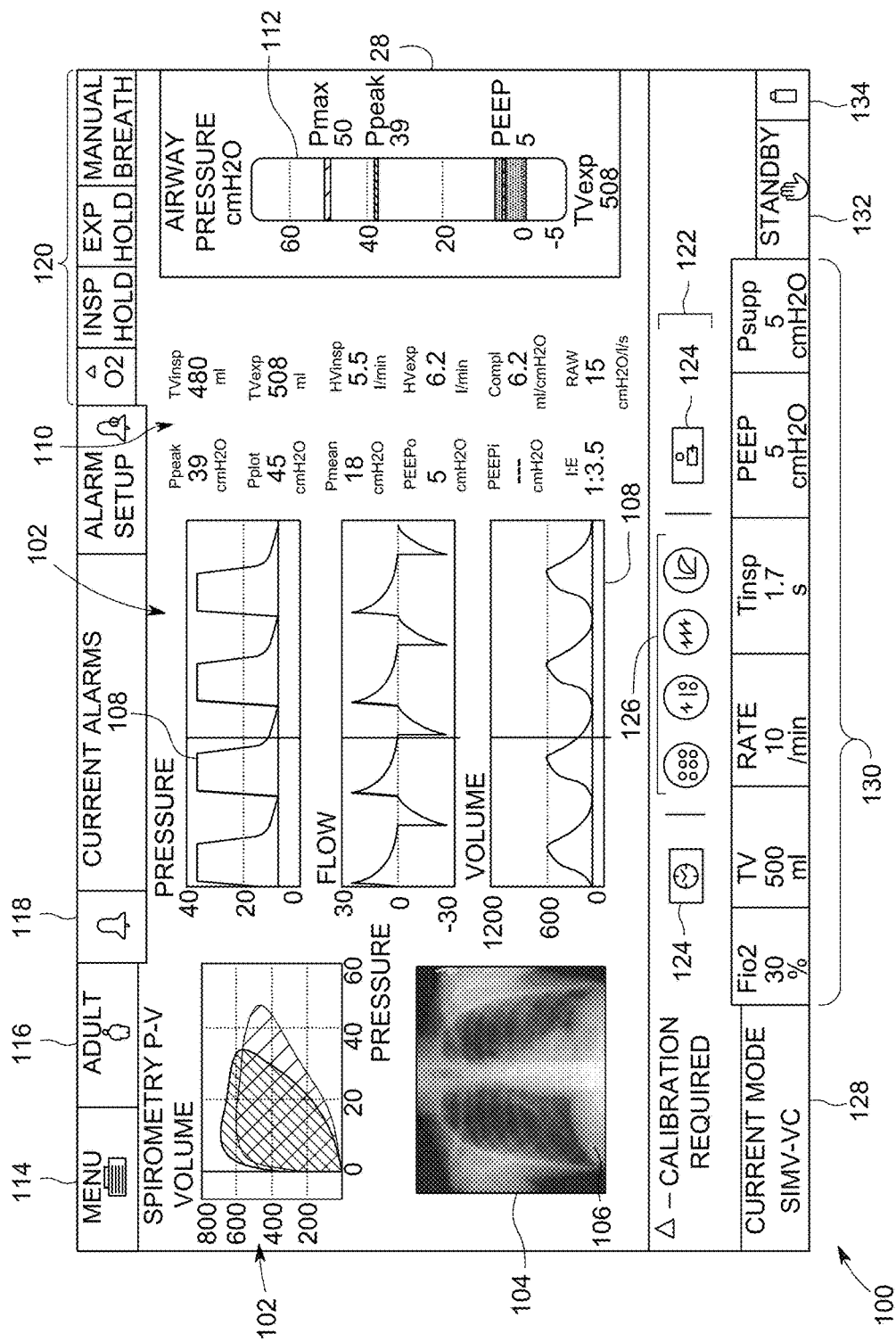
FIG. 7 illustrates a screen on a life support display showing a user interface in accordance with an embodiment.

More specifically, FIG. 7 illustrates a screenshot of a display 100 formed in accordance with an embodiment. In this embodiment, the display 100 is embodied as of displays the UI 28, which may be displayed on the LSS 20, for example, on the monitor 48 of the ventilator 42. In one exemplary embodiment, the display 100 is a touch screen display. Alternatively, the display 100 may be coupled to a user input device, for example, a keyboard, a mouse, or the like that may form part of the operator interface 46 (shown in FIG. 2). FIG. 7 generally illustrates LSS information display portions 102 and a non-LSS information display portion 104 (although more than one can be provided), which in this embodiment is shown as an image window. The non-LSS information display portion 104 in this embodiment illustrates the display of an x-ray image 106 of the patient. As can be seen, LSS information and non-LSS information may be displayed simultaneously or concurrently. It should be noted that the user may adjust the configuration of the displayed information, such as using a configuration menu.

The display 100 provides viewing and/or visualization of LSS information and non-LSS information that may facilitate controlling operation of the LSS 20. In various embodiments the LSS information display portions 102 generally display patient ventilator parameters that may be used to analyze and communicate recorded information and events related to the patient ventilator parameters. The LSS information may include currently available or real-time information or information obtained in the past, such as LSS measurements. For example, the LSS information display portions 102 may display current or past measurements of patient ventilator parameters (e.g. respiration rate, heart rate, blood pressure level, volume of breath, or the like), alarms that are occurring or have occurred in the past (e.g. measured patient ventilator parameters, device problems, or the like), events that have occurred in the past (e.g. changes in device settings, therapeutic processes, or the like), or recordings of system status that have occurred in the past (e.g. screen shots, periods of data recordings, or the like). The display 100 may include user selectable variations on the layout of measured patient values and corresponding graphic representations.

Thus, the LSS information display portions 102 display visualizations of patient ventilator parameters or measurements. For example, in the illustrated embodiment, several graphs 108 of ventilator measurements, such as mechanical ventilation measurements, including pressure, flow and volume are displayed. Measurement values or other numerical values 110 also may be displayed corresponding to the measurements, which may include, for example, average or peak measurement values or parameter settings.

Additional types of information also may be displayed. For example, in one embodiment, a scale 112 is displayed that represents an airway pressure of the patient. The scale 112 may be toggled on and off by an operator. The scale 112 may be provided, for example, as described in co-pending application Ser. No. 13/112,870, entitled "METHOD AND SYSTEM FOR VISUALIZING VENTILATION INFORMATION", and commonly owned.

A menu button 114 is provided for selecting a menu, for example, a menu screen or drop down menu that enables the operator to update and/or change various parameters of the display 100, as well as select between different types of information to display including to access and display different types of non-LSS information by selecting a corresponding stored image or file (e.g., a store directory may be accessed). A patient button 116 is provided for selecting a type of patient, for example, adult, child, or infant. Various operating parameters may be updated based on the type of patient. Additionally, various compliance ranges may updated based on the type of patient. An alert screen button 118 is activated to display current alert notifications. The alert notifications may also be accompanied by visual and/or audible alarms. In one embodiment, the alert screen button 118 may activate a drop down screen that displays the most recent alerts. Function buttons 120 also may be provided to instruct the ventilator to perform various functions. It should be noted that although the various buttons are shown as user selectable soft keys (e.g. user electable virtual buttons displayed on the screen), the buttons may be any type of hard or soft button, key, etc.

A toggle control portion 122 also may be provided to change the display 100, such as to toggle between displays showing different types of information such as past and present information using the buttons 124. For particular types of information, a set of buttons 126 may be provided to change the view of format of the displayed information.

A mode button 128 may be selected to change and/or update an operating mode of the ventilator. Parameter buttons 130 display desired compliance levels for various parameters. The parameter buttons 130 may be selected to alter the corresponding compliance levels. A standby button 132 may be selected to pause operation of the ventilator. Operation of the ventilator may be paused during various patient treatments, for system calibration, or the like. A battery display 134 indicates a battery level of at least one of the display 100 and/or the ventilator 42.

It should be noted that although the embodiments are described with respect to various functional buttons, not all of the functional buttons may be displayed or may be provided to practice the embodiments described herein. Additionally, various other functional buttons may be included on the display 100.

Figure 8:
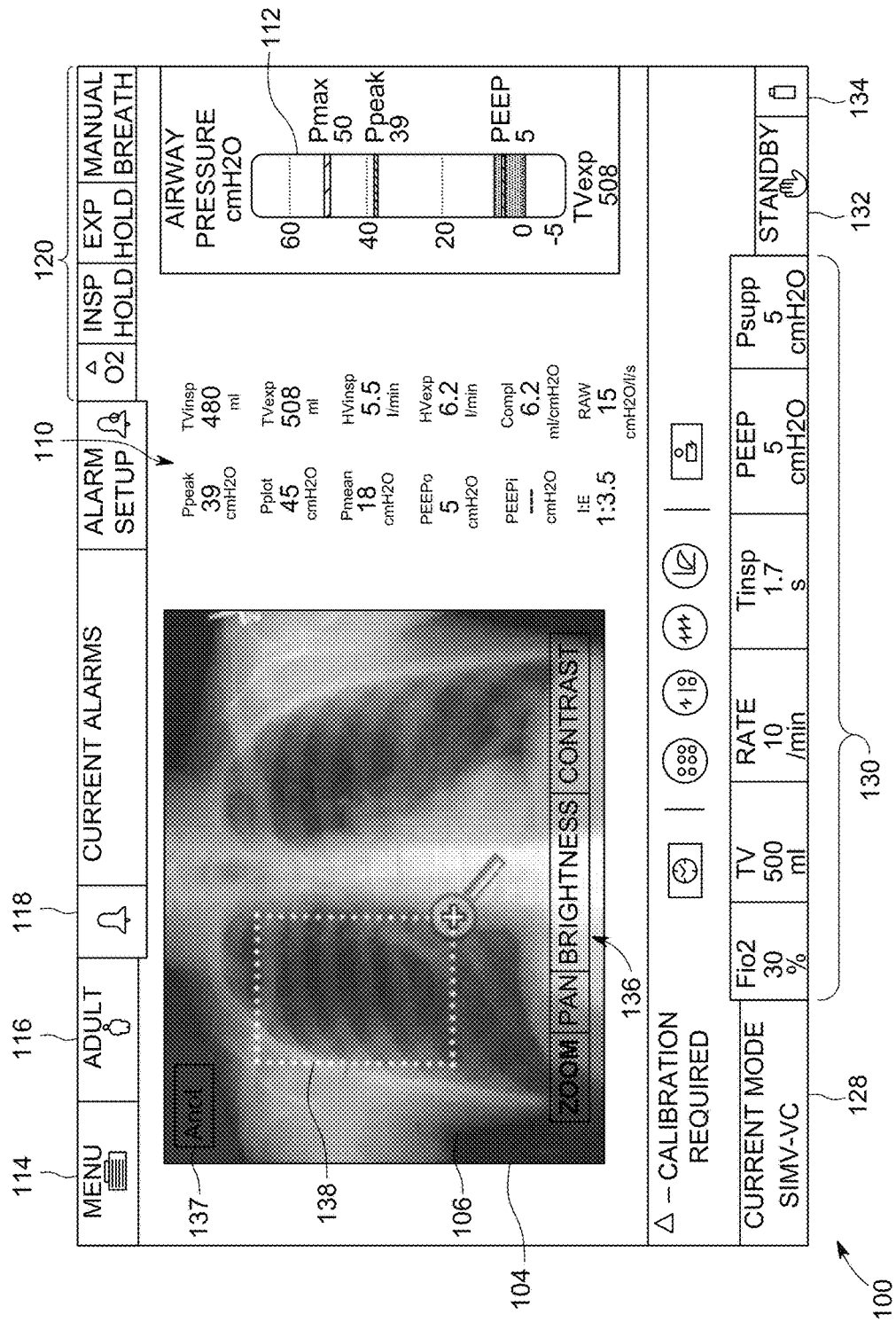
FIG. 8 illustrates a screen on a life support display showing a user interface in accordance with another embodiment.

Accordingly, the non-LSS information is displayed and may be reviewed directly using the LSS 20. In the illustrated embodiment, the non-LSS image is patient x-ray image(s). In some embodiments, the user may move or modify the non-LSS information display portion 104, such as by dragging the window to another location on the display 100 or by dragging an edge of the window to resize the window as shown in FIG. 8. The moved or resized non-LSS information display portion 104 may cause other portions of the display 100 to be automatically adjusted, for example, moved or adjusted, or may cover or overlay that information (which in this embodiment covers or replaces the graphs 108). A user may also open the non-LSS information display portion 104 on another screen, such as by selecting the non-LSS information display portion 104, for example, by double clicking the image 106 with a mouse or trackball of the operator interface 46. The LSS information and non-LSS information then may be displayed on separate screens, which a user may toggle between using a keyboard, a knob, or the like.

The non-LSS information display portion 104 provides additional options, such as by clicking on the image, which in some embodiments provides additional tools, shown as review buttons 136. The buttons 136 may provide for additional functionality, such as zoom, pan, tilt and/or adjust image settings, for example, brightness and/or contrast. The illustrated display 100 shows the zoom function as selected, which allows for enlarging or zooming in on a portion of the image 106 defined within a region 138 (e.g., selected with a resizable outline, which may take different shapes). Additionally, other functionality may be provided. For example, an annotation button 137 may be provided to allow for annotation of the image 106, such as to add text or graphics to the image 106.

Figure 9:
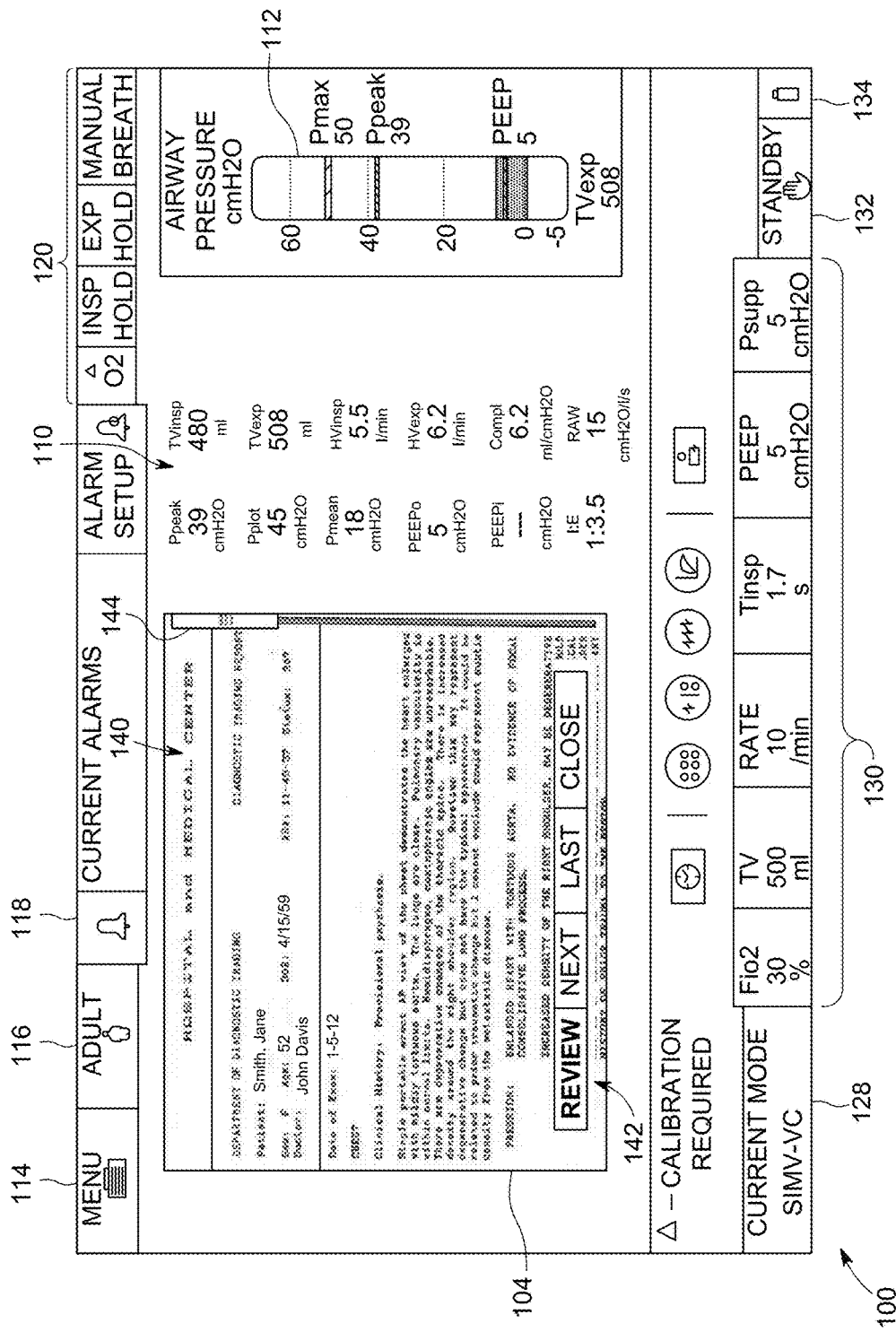
FIG. 9 illustrates a screen on a life support display showing a user interface in accordance with another embodiment.

In various embodiments, other types of non-LSS information may be displayed, which may or may not be images. For example, as shown in FIG. 9, the non-LSS information is text, such as a medical report, which is illustrated as a radiologist's report 140, which may correspond to the x-ray image 106 (shown in FIGS. 7 and 8). In this embodiment, the radiologist's report 140 within the non-LSS information display portion 104 covers a portion of the LSS information, such as covering or replacing the graphs 108. However, the window corresponding to the non-LSS information display portion 104 may be resized or moved to allow viewing of different parts of the non-LSS information display portion 104. The radiologist's report 140 may be selected similar to the image(s), such as using the menu button 114. Additionally, the non-LSS information display portion 104 when displaying the images or text, such as the radiologist's report 140, may also provide additional options or tools, shown as navigation buttons 142. The buttons 142 may provide additional functionality, such as to allow switching between different reports and also scrolling within a report, such as with a scroll bar 144. The radiologist's report 140 may be displayed on a separate screen and also may be displayed on the same screen as the x-ray image 106 in some embodiments, such as in a side-by-side configuration.

Thus, various embodiments provide an interface to display different types of information using an LSS. The interface allows for the visualization of information acquired by the LSS or parameters being controlled by the LSS, as well as information acquired or determined using different devices, such as an imaging scanner or other monitor.

It should be noted that the various embodiments, for example, the modules described herein, may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive, optical disk drive, solid state disk drive (e.g., flash drive of flash RAM) and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs, a program module within a larger program or a portion of a program module or a non-transitory computer readable medium. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A portable and stand-alone ventilation device configured to provide mechanical ventilation to a monitored patient, the ventilation device comprising:
    a ventilator configured to be operated using patient ventilation parameters to provide mechanical ventilation to the monitored patient;
    a patient monitoring portion configured to be operably coupled to one or more physiological monitoring sensors configured to acquire physiological information from the monitored patient, the patient monitoring portion configured to acquire, as ventilator monitoring information, patient measurement information from the monitored patient transmitted from the one or more physiological monitoring sensors;
    a communication device configured to communicate with a stand-alone imaging device to obtain imaging information acquired by the stand-alone imaging device, wherein the communication device communicates with the stand-alone imaging device via direct device-to-device communication to obtain the imaging information; and
    a ventilator user interface mounted to the ventilation device, the ventilator user interface configured to display the ventilator monitoring information, to display the patient ventilation parameters used by the ventilator to provide mechanical ventilation, to display the imaging information obtained via the stand-alone imaging device, and to control the ventilation parameters for operating the ventilator to provide mechanical ventilation to the monitored patient, wherein the ventilator user interface provides the ventilator monitoring information, patient ventilation parameters, and imaging information to an operator and controls the operation of the ventilator to provide mechanical ventilation responsive to input received from the operator.

2. The ventilation device of claim 1, wherein the ventilator user interface is configured to display the ventilator monitoring information and the imaging information concurrently.

3. The ventilation device of claim 1, wherein the ventilator monitoring is displayed as at least one of one or more graphs or one or more measurement values.

4. The ventilation device of claim 1, further comprising an imaging information display portion for displaying the imaging information, the imaging display portion defining a window on the display.

5. The ventilation device of claim 4, wherein the window is one of sizeable or movable on the display.

6. The ventilation device of claim 1, further comprising user selectable members presented on the display and operable to control at least one of review functions or navigation functions for the imaging information display portion.

7. The ventilation device of claim 6, wherein the review functions include annotations functions to annotate the displayed imaging information.

8. The ventilation device of claim 1, wherein the imaging information comprises an x-ray image.

9. The ventilation device of claim 1, wherein the imaging information comprises a radiologist's report.

10. The ventilation device of claim 1, wherein the imaging information comprises an Electronic Medical Record.

11. The ventilation device of claim 1, wherein the imaging information comprises a lab report.

12. The ventilation device of claim 1, further comprising a memory for storing the imaging information.

13. The ventilation device of claim 1, wherein the ventilation device is further configured to prompt the operator to transfer the imaging information from the stand-alone imaging device to the ventilation device before the operator leaves a room in which the ventilation device is disposed.

14. The ventilation device of claim 1, further comprising a data access module to acquire the imaging information.

15. A method for presenting data using a portable and stand-alone ventilation device including a ventilator, the method comprising:
    providing, with the ventilator, mechanical ventilation to a patient using patient ventilation parameters;
    receiving, by the ventilation device, as ventilator monitoring information, physiological information from one or more physiological monitoring sensors operably coupled to the patient;
    receiving by the ventilation device, as imaging information, information from a stand-alone imaging device, wherein the imaging information is acquired by the stand-alone imaging device and received from the stand-alone imaging device by the ventilation device via direct device-to-device communication with the stand-alone imaging device to obtain the imaging information;
    providing access to the imaging information via the ventilation device;

displaying the imaging information, the ventilator monitoring information, and the patient ventilation parameters on a ventilator user interface mounted to the ventilation device; and controlling the ventilator using a manual input provided by an operator viewing the ventilator monitoring information, the imaging information, and the patient ventilation parameters on the ventilator user interface.

16. The method of claim 15, further comprising displaying ventilator monitoring information acquired by the ventilation device concurrently with the imaging information.

17. The method of claim 15, wherein the imaging information comprises a medical report.

18. The method of claim 15, further comprising receiving a user input annotating the displayed imaging information.

19. The method of claim 15, further comprising storing the imaging information in a memory of the ventilation device.

20. The method of claim 15, further comprising prompting the operator to transfer the imaging information from the stand-alone imaging device to the ventilation device before leaving a room in which the ventilation system and stand-alone imaging device are disposed.

21. A non-transitory computer readable storage medium for displaying information with a portable and stand-alone ventilation device using a processor, the ventilation device including a ventilator, the non-transitory computer readable storage medium including instructions to command the processor to:

provide, with the ventilator, mechanical ventilation to a patient using patient ventilation parameters;

receive, by the ventilation device, as ventilator monitoring information, physiological information from one or more physiological monitoring sensors operably coupled to the patient;

receive by the ventilation device, as imaging information, information from a stand-alone imaging device, wherein the imaging information is acquired by the stand-alone imaging device and received from the stand-alone imaging device by the ventilation device via direct device-to-device communication with the stand-alone imaging device to obtain the imaging information;

provide access to the imaging information via the ventilation device;

display the imaging information, the ventilator monitoring information, and the patient ventilation parameters on a display of a ventilator user interface mounted to the ventilation device; and control the ventilator using a manual input provided by an operator viewing the ventilator monitoring information, the imaging information, and the patient ventilation parameters on the ventilator user interface.

22. The non-transitory computer readable storage medium of claim 21, wherein the instructions further command the processor to display ventilator monitoring information acquired by the ventilation device concurrently with the imaging information.

23. The non-transitory computer readable storage medium of claim 21, wherein the imaging comprises a medical report.

24. The non-transitory computer readable storage medium of claim 21, wherein the instructions further command the processor to receive a user input annotating the displayed imaging information.

25. The non-transitory computer readable storage medium of claim 21, wherein the instructions further command the processor to store the imaging information in a memory of the ventilation device.

* * * * *